(12) United States Patent
Kock

(10) Patent No.: US 6,349,723 B1
(45) Date of Patent: Feb. 26, 2002

(54) ANAESTHETIC MACHINE

(75) Inventor: Mikael Kock, Akersberga (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/495,712

(22) Filed: Feb. 1, 2000

(30) Foreign Application Priority Data

Feb. 4, 1999 (SE) .......................................... 9900368-3

(51) Int. Cl.$^7$ ...................... A61M 16/00; A61M 16/01; A61M 16/08

(52) U.S. Cl. ............................ 128/203.28; 128/203.12; 128/203.14; 128/204.28; 128/205.13; 128/205.14; 128/205.24

(58) Field of Search ....................... 128/203.12, 203.14, 128/203.26, 203.27, 203.28, 204.28, 205.13, 205.14, 205.24

(56) References Cited

U.S. PATENT DOCUMENTS

| | | |
|---|---|---|
| 4,023,587 A | 5/1977 | Dobritz |
| 4,224,940 A | 9/1980 | Monnier |
| 4,401,115 A | 8/1983 | Monnier |
| 5,315,989 A | 5/1994 | Tobia |
| 5,497,767 A * | 3/1996 | Olsson et al. .......... 128/205.13 |
| 5,509,406 A * | 4/1996 | Kock et al. ............ 128/203.14 |
| 5,678,540 A * | 10/1997 | Kock et al. ............ 128/205.13 |
| 5,687,709 A * | 11/1997 | Akerberg ............... 128/203.12 |
| 5,694,924 A * | 12/1997 | Cewers .................. 128/204.21 |
| 5,699,788 A * | 12/1997 | Lekholm et al. ....... 128/203.12 |
| 5,771,882 A * | 6/1998 | Psaros et al. .......... 128/203.12 |
| 5,806,513 A | 9/1998 | Tham et al. |
| 6,032,665 A * | 3/2000 | Psaros .................. 128/203.12 |
| 6,155,256 A * | 12/2000 | Wallin .................. 128/203.16 |

FOREIGN PATENT DOCUMENTS

DE    OS 29 45 472    5/1981

* cited by examiner

Primary Examiner—John G. Weiss
Assistant Examiner—Mital Patel
(74) Attorney, Agent, or Firm—Schiff Hardin & Waite

(57) ABSTRACT

An anaesthetic machine has a gas flow system with a variable-volume gas container for breathing gas, a fresh gas system for supplying the fresh gas system with a flow of fresh gas and a control unit. The control unit controls the variable-volume gas container during a first phase of inspiration so that a flow of breathing gas is released and mixes with a flow of fresh gas from the fresh gas system. The control unit starts a second phase of inspiration if the flow of breathing gas from the variable-volume gas container ceases before inspiration has been completed. The control unit controls the anaesthetic machine during said second phase so that inspiration is maintained with a flow of fresh gas from the fresh gas system in order to achieve a system in which all breathing modes can be accommodated and gas consumption is minimized.

9 Claims, 1 Drawing Sheet

ANAESTHETIC MACHINE

BACKGROUND OF THE INVENTION

1. Field of the Invention

The present invention is directed to an anaesthetic machine of the type having a gas flow system with a variable-volume gas container for breathing gas, a fresh gas system for supplying a flow of fresh gas to the gas flow system, and a control unit which controls the variable-volume gas container during a first phase of inspiration so that a flow of breathing gas is released and mixes with a flow of fresh gas from the fresh gas system.

2. Description of the Prior Art

Anaesthetic machines usually operate in a manner referred to as volume-controlled modes, i.e. they are devised to supply a specific tidal volume of breathing gas to a patient in every breathing cycle. This can be achieved by utilization of a variable-volume gas container whose volume corresponds to the tidal volume. The gas container can be a piston or a bellows that is mechanically restricted to the specific tidal volume. One such system is described in German OS 29 45 472.

Anaesthetic machines that are also capable of operating in pressure-controlled modes have been described, e.g. in U.S. Pat. No. 5,315,989. Here, the variable-volume gas container is an unrestricted bellows. The pressure of drive gas applied to the exterior of the bellows is regulated in order to maintain a specific inspiratory or expiratory pressure.

A fresh gas is usually also introduced downstream from the variable-volume gas container. This flow of fresh gas is usually constant and continuous. The flow of fresh gas naturally has an impact on the flow of gas from the variable-volume gas container. The volume of this fresh gas must be compensated in the volume-control mode.

Since gases are compressible, minimizing the volume of gas in the anaesthetic machine is desirable. Moreover, anaesthetic agents are generally expensive, so minimizing the consumption of gas in the anaesthetic machine is also desirable.

Known commercial systems are unable to achieve these advantages.

SUMMARY OF THE INVENTION

An object of the present invention is accordingly to achieve an anaesthetic machine which is capable of operating in all known ventilation modes, without any real limitations, for both anaesthesia and intensive care, especially in the pressure-controlled mode.

Another object of the invention is to achieve an anaesthetic machine that solves the aforementioned gas consumption problems.

The above object is achieved in accordance with the principles of the present invention in an anaesthetic machine of the type initially described wherein the control unit starts a second phase of inspiration if the flow of breathing gas from the variable-volume gas container ceases before inspiration is completed, and in this second phase the control unit controls the anaesthetic machine so that inspiration is maintained by a flow of fresh gas from the fresh gas system.

A number of advantages is achieved by the invention. Among other things, a smaller volume can be kept in the gas container, with no risk of the patient running out of gas or of any failure of the breathing mode to operate as intended. If, during the first phase of inspiration, gas flow from the variable-volume gas container ceases, a control unit operates to switch operation to a second phase of inspiration. During the second phase inspiration is maintained by gas from the fresh gas system only.

In principle, flow from the variable-volume gas container could cease for two different reasons. One is because no more gas remains in the variable-volume container (minimized system) or because the flow of fresh gas is large enough to sustain inspiration, whereupon flow from the variable-volume gas container has been stopped by the control unit.

The former would be more common in systems wherein a control unit in the anaesthetic machine controls flows from both the variable-volume container and the fresh gas source.

The latter would be more common in systems wherein the setting of a continuous flow of fresh gas is manually controlled by a physician. The control unit would then control flow of gas in other parts of the anaesthetic system for maintaining set inspiration characteristics.

Any surplus breathing gas can be used to fill the gas container. The patient therefore receives a larger percentage of breathing gas in the next breathing cycle.

If the gas container becomes completely filled during the second phase before inspiration has concluded, the surplus can be evacuated during a third phase.

If the flow of gas into the patient increases during the second or third phase of inspiration so the flow of fresh gas is not enough to sustain inspiration, the anaesthetic machine can revert to the first phase and supply gas from the gas container.

The anaesthetic machine can be regulated in numerous ways in order to achieve the effects of the second and third phases.

One way is to devise a control unit to exercise active control of the flow of fresh gas so this flow is big enough (to sustain inspiration and possibly even fill the gas container to a specific volume).

Another way is to arrange one or more valves at strategic locations in the anaesthetic machine, preferably at the gas container, and to regulate them so as to maintain inspiration. The flow of fresh gas could then be allowed to remain constant and (possibly) continuous.

The anaesthetic machine according to the invention is especially suitable for use in pressure-controlled modes, whereby a pressure gauge is applied to or near the patient in order to measure patient pressure.

DESCRIPTION OF THE PREFERRED EMBODIMENTS

Figure 1:
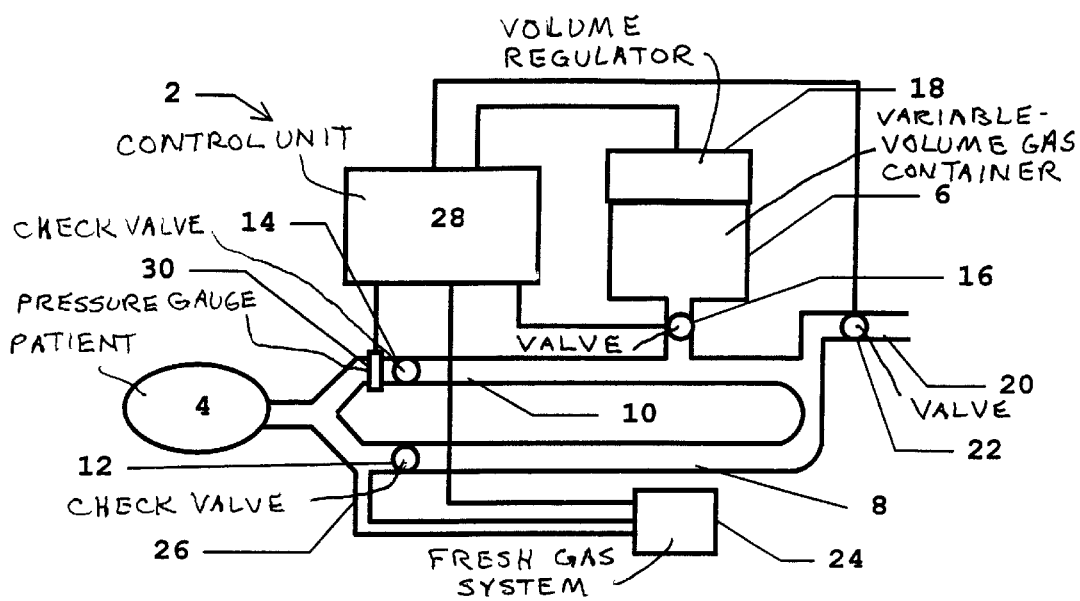
FIG. 1 shows a first embodiment of the anaesthetic machine according to the invention.

A first embodiment of the anaesthetic machine according to the invention is shown in FIG. 1 and designated 2. The anaesthetic machine 2 is connected to a patient 4 for the purpose of anaesthetizing her/him.

The anaesthetic machine 2 has a variable-volume gas container 6 that constitutes, with an inspiratory line 8 and an expiratory line 10, a gas flow system in the anaesthetic machine 2.

The gas container can be a bellows, piston or some other variable-volume container. They are well known in the anaesthesia art and require no further description in this context.

A first check valve 12 is arranged in the inspiratory line 8, and a second check valve 14 is arranged in the expiratory line 10. The task of the check valves 12, 14 is to control the direction of gas flow in the gas flow system. A fan can be used as an alternative to check valves 12, 14 in controlling the direction of gas flow.

A first adjustable valve 16 is arranged in the connection between the gas container 6 and the inspiratory line 8 and the expiratory line 10. The function of this first valve 16 is described below in greater detail. The volume of the gas container 6 is regulated by a volume regulator 18. When a piston is used, the volume regulator 18 can be a motor for regulating the position of the piston. When the gas container 6 is a bellows, the regulator 18 can contain a drive gas system for pressure interaction with the gas inside the bellows or a mechanical system for changing the position of the bellows.

Gas can be carried out of the gas flow system through an evacuation line 20. A second valve 22 is arranged in the evacuation line 20 and is described below in greater detail.

Fresh gas can be added to the gas flow system from a fresh gas system 24 through a fresh gas line 26. In principle, fresh gas can be added in any way, i.e. continuously, intermittently, variably etc.

The anaesthetic machine 2 is controlled by a control unit 28 connected to all adjustable units. The anaesthetic machine 2 is controlled via programmable breathing modes selected by the attending physician and by parameters measured in the anaesthetic machine 2. One such parameter is pressure. It can be measured by a pressure gauge 30. In this embodiment the pressure gauge 30 is arranged close to the patient 4 to measure patient pressure. Other pressure gauges, as well as flow meters, thermometers or other gauges used in the known fashion for monitoring or controlling the anaesthetic machine 2, can be arranged at other locations in the anaesthetic machine 2.

A specific function of the anaesthetic machine 2 according to the invention will be described below. In order to facilitate this description, it is assumed that the fresh gas system 24 is set to deliver a continuous and constant flow of fresh gas and that the pressure-controlled mode is set.

At the beginning of an inspiration, the gas container 6 supplies a flow of gas which, with the flow of fresh gas, generates a specific gas pressure pre-set for the patient 4. The gas container 6 is controlled to maintain this gas pressure. This constitutes a first phase of inspiration.

If the flow of gas into the patient 4 abates so the flow of fresh gas is in itself sufficient for maintaining the pre-set gas pressure, the flow of gas from the container 6 ceases completely. This constitutes a second phase in inspiration.

Since the flow of fresh gas is constant, a surplus of gas could develop that must be diverted to keep the pressure from rising.

In accordance with the invention, the gas container 6 is regulated so any surplus fresh gas is sent to it. The gas container 6 therefore will fill with fresh gas during ongoing inspiration, which was not possible in conventional devices. The pressure can be maintained when the first valve 16 and the volume regulator 18 are controlled so the influx of gas into the container 6 occurs in a way enabling pressure to be maintained in respect to the patient 4.

If the gas container 6 becomes full, inspiration moves into a third phase in which surplus gas is carried via the second valve 22 through the evacuation line 20 to a gas evacuation unit. If this third phase occurs too frequently, it is a sign that the flow of fresh gas is excessive. Information to this effect then can be shown on a display with a recommendation as to a reduction in the flow. Alternatively, the flow of fresh gas can be reduced automatically.

If the flow into the patient 4 should suddenly exceed the flow of fresh gas during the second or third phase, the anaesthetic machine 2 reverts to the first phase and supplies requisite gas from the gas container 6.

A system with a low total consumption of gas and a minimal compressible volume in the gas flow system can be achieved by adapting the pre-set parameters in the proper fashion.

In instances in which the fresh gas system 24 is only intended to supply a continuous and constant flow of gas, the fresh gas system 24 does not need to be controlled by the control unit 28. The fresh gas system 24 then can be completely manual.

The above description also applies to volume-control and other operating modes.

Figure 2:
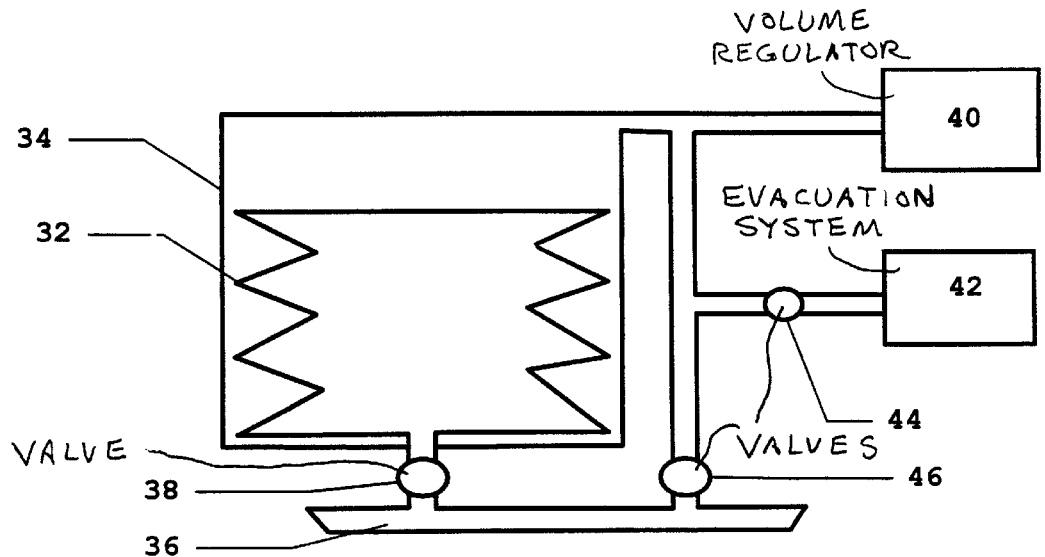
FIG. 2 shows a part of the anaesthetic machine according to a second embodiment.

FIG. 2 shows part of a second embodiment of the anaesthetic machine according to the invention, i.e. a gas container in the form of a bellows 32 arranged inside a gas-tight enclosure 34. The interior of the bellows 32 is connected to the gas line 36 via a first valve 38. The gas line 36 can be an inspiratory line or an expiratory line.

A volume regulator 40 is connected to the enclosure 34 in order to affect the pressure of the gas inside the bellows 32. The volume regulator 40 can be in the form of e.g. an adjustable source of gas.

An evacuation system 42 is connected to the container 34 via a second valve 44, and the gas line 36 is connected to the evacuation system 42 via a third valve 46.

During the first phase of inspiration, as described above, gas at a specific pressure is fed into the enclosure 34 in order to compress the bellows 32. The first valve 38 is open, and a flow of gas is accordingly sent to the gas line 36.

During the second phase, gas supplied by the volume regulator 40 is cut off. The first valve 38 is closed at the same time as the second valve 44 is opened to allow the passage of gas from the container 34 to the evacuation system 42. The second valve 44 can then be regulated to keep the drop in pressure in the container 34 from becoming excessive. This is to enable rapid re-delivery of gas from the bellows 32.

If the gas line 36 contains a surplus of fresh gas, the first valve 38 is regulated so the surplus is fed into the bellows 32. The bellows 32 is able to expand, since pressure on its exterior (inside the enclosure 34) has been reduced. Alternately, the second valve 44 can be regulated at the same time as the first valve 38 to make sure the surplus is fed into the bellows 32.

If the third phase becomes necessary, the first valve 38 is closed and the third valve 46 is opened to pass surplus gas straight into the evacuation system 42.

The anaesthetic machine according to the invention has been described for two embodiments, however, the inventive concept is applicable to virtually all known anaesthetic machines, after requisite modification for maintaining inspiration with a flow of fresh gas alone.

This could occur when the gas container is empty or when the need for flow in the gas flow system is met by the flow of fresh gas.

Although modifications and changes may be suggested by those skilled in the art, it is the intention of the inventor to embody within the patent warranted hereon all changes and modifications as reasonably and properly come within the scope of his contribution to the art.

I claim as my invention:

1. An anaesthetic machine comprising:

a gas flow system including a variable-volume gas container which contains breathing gas;

a fresh gas system which supplies a flow of fresh gas to said gas flow system; and a control unit for controlling said variable-volume gas container during a first phase of inspiration to release a flow of breathing gas from said variable-volume gas container for mixing with said flow of fresh gas from said fresh gas system, and for starting a second phase of inspiration if said flow of breathing gas from the variable-volume gas container ceases before a completion of inspiration, and said control unit during said second phase maintaining inspiration only by a flow of fresh gas from said fresh gas system.

2. An anaesthetic machine as claimed in claim 1 wherein said control unit controls said variable-volume gas container during said second phase to cause any surplus flow of fresh gas from said fresh gas system to be sent to said variable-volume gas container.

3. An anaesthetic machine as claimed in claim 2 further comprising an evacuation system, and wherein said control unit starts a third phase of inspiration if said variable-volume gas container becomes filled before said completion of inspiration, said control unit during said third phase causing any surplus flow of fresh gas from said fresh gas system to be sent to said evacuation system for removal of said surplus gas from said gas flow system.

4. An anaesthetic machine as claimed in claim 3 wherein said fresh gas system supplies a continuous flow of fresh gas to said gas flow system, and said anaesthetic machine further comprising a first valve at said variable-volume container which regulates gas flow to and from said gas container, and a second valve at said evacuation system to regulate the flow of gas to said evacuation system.

5. An anaesthetic machine as claimed in claim 4 wherein said fresh gas system supplies a constant flow of fresh gas.

6. An anaesthetic machine as claimed in claim 2 wherein said control unit reverts to control in said first phase if said flow of fresh gas from said fresh gas system becomes inadequate.

7. An anaesthetic machine as claimed in claim 1 wherein said control unit controls delivery of fresh gas from said fresh gas system to said gas flow system.

8. An anaesthetic machine as claimed in claim 1 further comprising at least one pressure gauge for determining pressure in said gas flow system and for supplying a signal identifying pressure in said gas flow system to said control unit, and wherein said control unit maintains a predetermined pressure in said gas flow system dependent on said signal.

9. An anaesthetic machine as claimed in claim 1 further comprising:

a tubing system adapted for connection to a patient and being connected to said variable volume gas container and to said fresh gas system, with said breathing gas and said flow of fresh gas being mixed in said tubing system;

said variable volume gas container having a volume regulator and an adjustable valve, said adjustable valve being connected between an outlet of said variable volume gas container and said tubing system; and said control unit controlling said volume regulator and adjusting said adjustable valve to maintain a predetermined pressure in said tubing system.

* * * * *